(12) United States Patent
Chaki et al.

(10) Patent No.: US 9,708,234 B2
(45) Date of Patent: Jul. 18, 2017

(54) PROCESS FOR PRODUCING FLUORINE-CONTAINING OLEFIN

(71) Applicant: DAIKIN INDUSTRIES, LTD., Osaka (JP)

(72) Inventors: Takehiro Chaki, Osaka (JP); Daisuke Karube, Osaka (JP); Masami Nishiumi, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 14/405,978

(22) PCT Filed: Jul. 10, 2013

(86) PCT No.: PCT/JP2013/069453
§ 371 (c)(1),
(2) Date: Dec. 5, 2014

(87) PCT Pub. No.: WO2014/010750
PCT Pub. Date: Jan. 16, 2014

(65) Prior Publication Data
US 2015/0148571 A1 May 28, 2015

Related U.S. Application Data

(60) Provisional application No. 61/669,817, filed on Jul. 10, 2012.

(51) Int. Cl.
*C07C 17/20* (2006.01)
*C07C 17/25* (2006.01)
(Continued)

(52) U.S. Cl.
CPC ............. *C07C 17/21* (2013.01); *B01J 23/26* (2013.01); *B01J 35/002* (2013.01); *B01J 35/026* (2013.01);
(Continued)

(58) Field of Classification Search
CPC ........ C07C 17/25; C07C 17/206; C07C 17/20
See application file for complete search history.

(56) References Cited

U.S. PATENT DOCUMENTS 5,710,352 A * 1/1998 Tung .............................. 570/166
7,230,146 B2 * 6/2007 Merkel et al. ................. 570/155
(Continued)

FOREIGN PATENT DOCUMENTS

JP WO 2011099605 A2 * 8/2011 ............. C07C 17/21
JP 2012-020992 2/2012
(Continued)

OTHER PUBLICATIONS

International Search Report issued Nov. 14, 2013 in International (PCT) Application No. PCT/JP2013/069453 along with the Written Opinion.
(Continued)

*Primary Examiner* — Medhanit Bahta
(74) *Attorney, Agent, or Firm* — Wenderoth, Lind & Ponack, L.L.P.

(57) ABSTRACT

The present invention provides a process for producing a fluoroolefin by reacting, in a gas phase, a fluorinating agent and a chlorine-containing alkene or a chlorine-containing alkane in the presence of at least one catalyst selected from the group consisting of chromium oxide, at least part of which is crystallized, and fluorinated chromium oxide obtained by fluorinating the chromium oxide. According to the present process, a target fluoroolefin can be obtained at a high conversion rate of the starting material and with high selectivity.

13 Claims, 2 Drawing Sheets

(51) Int. Cl.
 *C07C 17/21* (2006.01)
 *B01J 37/03* (2006.01)
 *B01J 23/26* (2006.01)
 *B01J 35/00* (2006.01)
 *B01J 35/02* (2006.01)
 *B01J 35/10* (2006.01)

(52) U.S. Cl.
 CPC ......... *B01J 35/1014* (2013.01); *B01J 37/031* (2013.01); *C07C 17/206* (2013.01); *C07C 17/25* (2013.01); *Y02P 20/582* (2015.11)

(56) References Cited

U.S. PATENT DOCUMENTS

| | | | |
|---|---|---|---|
| 9,388,099 B2* | 7/2016 | Takahashi | C07C 17/206 |
| 2005/0228202 A1* | 10/2005 | Nappa et al. | 570/161 |
| 2010/0072415 A1* | 3/2010 | Rao et al. | 252/67 |
| 2010/0210882 A1* | 8/2010 | Sharratt et al. | 570/142 |
| 2012/0078020 A1 | 3/2012 | Elsheikh et al. | |

FOREIGN PATENT DOCUMENTS

| | | |
|---|---|---|
| WO | 2007/079431 | 7/2007 |
| WO | 2007/079435 | 7/2007 |
| WO | 2008/002500 | 1/2008 |
| WO | 2008/060614 | 5/2008 |
| WO | 2009/125199 | 10/2009 |
| WO | 2010/013796 | 2/2010 |
| WO | 2010/035748 | 4/2010 |
| WO | 2012/057367 | 5/2012 |

OTHER PUBLICATIONS

Z. Xie et al., "Cr2O3 Catalysts for Fluorination of 2-Chloro-3,3,3-trifluoropropene to 2,3,3,3-Tetrafluoropropene", Industrial and Engineering Chemistry Research, vol. 52, No. 9, pp. 3295-3299, 2013.

Japanese Office Action issued Dec. 8, 2015 in corresponding Japanese Patent Application No. 2014-558350 with Machine Translation.

* cited by examiner

PROCESS FOR PRODUCING FLUORINE-CONTAINING OLEFIN

TECHNICAL FIELD

The present invention relates to a process for producing fluorine-containing olefin.

BACKGROUND ART

Fluoroolefins represented by the formula: $CF_3(CX_2)_nCF=CH_2$, the formula: $CF_3(CX_2)_nCH=CHF$, or the like, are compounds that have a useful structure as various functional materials, solvents, refrigerants, blowing agents, and monomers for functional polymers or starting materials of such monomers. For example, fluoroolefins are used as monomers for modifying ethylene-tetrafluoroethylene copolymers. Further, of the fluoroolefins mentioned above, the compound represented by $CF_3CF=CH_2$ (HFO-1234yf) and the compound represented by $CF_3CH=CHF$ (HFO-1234ze) have recently gained attention because they offer promising prospects as refrigerants with low global-warming potential.

As one of the processes for producing fluoroolefins represented by the formulae above, many methods have been reported regarding a process in which a starting material chlorine-containing alkane or chlorine-containing alkene having the same number of carbon atoms as that of a target fluoroolefin is reacted with a fluorinating agent such as an anhydrous hydrogen fluoride in the presence of a catalyst (Patent Literature 1 to 6). In this process, a chromium oxide catalyst, antimony catalyst, or the like is used as a catalyst. In particular, it has been reported that an amorphous chromium oxide catalyst is effective (Patent Literature 6). Further, when an amorphous chromium oxide catalyst is used, a method of entraining $O_2$ or the like with a reactant to maintain the catalyst activity has been reported. However, in this method, a side reaction of the entrained $O_2$ with the reactant sometimes produces $CO_2$ as a by-product, or produces several by-products other than $CO_2$, which cannot be converted into target products. This causes problems such as a decrease in the yield of target fluoroolefin, complications in a purification step, and a rise in the costs of the equipment used in the purification step.

CITATION LIST

Patent Literature

PTL 1: WO 07/079435
PTL 2: WO 07/079431
PTL 3: WO 08/002500
PTL 4: WO 08/060614
PTL 5: WO 09/125199
PTL 6: WO 10/013796

SUMMARY OF INVENTION

Technical Problem

The present invention is made in light of the current state of the technical field as mentioned above, and a main object is to provide a process for producing fluoroolefins by reacting a fluorinating agent with a chlorine-containing alkane or a chlorine-containing alkene, which is used as a starting material, the process being capable of efficiently producing fluoroolefins by improving the conversion rate of the starting material and inhibiting the generation of impurities, which cause problems in separation and yield.

Solution to Problem

The present inventors conducted extensive research to achieve the above object. As a result, they found the following. When a chromium oxide catalyst, at least part of which is crystallized, or a catalyst obtained by fluorinating the chromium oxide catalyst is used to produce a fluoroolefin compound by reacting a fluorinating agent with a chlorine-containing alkane represented by a specific formula or a chlorine-containing alkene represented by a specific formula, which is used as a starting material, the conversion rate of the starting material is improved, and the selectivity of the target fluoroolefin is increased, which allows efficient fluoroolefin production. In particular, by adjusting the crystallite diameter of the chromium oxide catalyst, or allowing the presence of a specific amount of oxygen during the reaction, the conversion rate of the starting material and the selectivity of the target fluoroolefin can be increased. The present invention was accomplished based on these findings.

Specifically, the present invention offers the following process for producing fluoroolefins.

Item 1. A process for producing a fluoroolefin comprising:
reacting a fluorinating agent and a chlorine-containing compound in a gas phase in the presence of at least one catalyst selected from the group consisting of chromium oxide, at least part of which is crystallized, and fluorinated chromium oxide obtained by fluorinating the chromium oxide, the chlorine-containing compound being at least one compound selected from the group consisting of a chlorine-containing alkane represented by formula (1): $CX_3(CX_2)_nCClYCH_2Z$, wherein each X is independently F or Cl, and Y is H or F, and when Y is H, Z is Cl or F, and when Y is F, Z is H, and n is an integer of 0 to 2; a chlorine-containing alkane represented by formula (2): $CX_3(CX_2)_nCH_2CHX_2$, wherein each X is independently F or Cl, at least one X is Cl, and n is an integer of 0 to 2; a chlorine-containing alkene represented by formula (3): $CX_3(CX_2)_nCCl=CH_2$, wherein each X is independently F or Cl, and n is an integer of 0 to 2; a chlorine-containing alkene represented by formula (4): $CX_3(CX_2)_nCH=CHX$, wherein each X is independently F or Cl, at least one X is Cl, and n is an integer of 0 to 2; and a chlorine-containing alkene represented by formula (5): $CH_2XCCl=CX_2$, wherein each X is independently F or Cl, the fluoroolefin to be obtained being a compound represented by formula (6): $CF_3(CF_2)_nCA=CHB$, wherein one of A and B is F and the other is H, and n is an integer of 0 to 2, provided that n is 0 when the chlorine-containing alkene represented by formula (5) is used as a starting material.

Item 2. The process for producing a fluoroolefin according to Item 1, wherein the chromium oxide, at least part of which is crystallized, has a crystallinity of 30% or more.

Item 3. The process for producing a fluoroolefin according to Item 1, wherein the chromium oxide, at least part of which is crystallized, has a crystallinity of 60% or more.

Item 4. The process for producing a fluoroolefin according to Item 1, wherein the chromium oxide, at least part of which is crystallized, has a crystallinity of 70% or more.

Item 5. The process according to any one of Items 1 to 4, wherein the chromium oxide has an average crystallite diameter of 50 nm or less.

Item 6. The process according to any one of Items 1 to 5, wherein the chromium oxide has a specific surface area of 10 $m^2/g$ or more.

Item 7. The process according to any one of Items 1 to 6, wherein a catalyst supported on a carrier is used.

Item 8. The process according to Item 7, wherein the carrier is at least one member selected from the group consisting of $SiO_2$, $Al_2O_3$, zeolite, activated carbon, and zirconium oxide.

Item 9. The process according to any one of Items 1 to 8, wherein the catalyst comprising the chromium oxide, at least part of which is crystallized, is fluorinated, and then the chlorine-containing compound is reacted with the fluorinating agent.

Item 10. The process for producing a fluoroolefin according to any one of Items 1 to 9, wherein the fluorinating agent is anhydrous hydrogen fluoride.

Item 11. The process for producing a fluoroolefin according to any one of Items 1 to 10, wherein the chlorine-containing compound used as a starting material is at least one member selected from the group consisting of a chlorine-containing alkane represented by formula (1): $CX_3(CX_2)_nCClYCH_2Z$, a chlorine-containing alkene represented by formula (3): $CX_3(CX_2)_nCCl=CH_2$, and a chlorine-containing alkene represented by formula (5): $CH_2XCCl=CX_2$, and the fluoroolefin to be obtained is a compound represented by formula (6-1): $CF_3(CF_2)_nCF=CH_2$, wherein n is an integer of 0 to 2, provided that n is 0 when the chlorine-containing alkene represented by formula (5) is used as a starting material.

Item 12. The process for producing a fluoroolefin according to Item 11, wherein the chlorine-containing compound used as a starting material is at least one member selected from the group consisting of $CF_3CHClCH_2Cl$ (HCFC-243db), $CCl_3CCl=CH_2$ (HCO-1230xf), $CF_3CCl=CH_2$ (HCFO-1233xf), and $CH_2ClCCl=CCl_2$ (HCO-1230xa), and the fluoroolefin to be obtained is $CF_3CF=CH_2$ (HFO-1234yf).

Item 13. The process for producing a fluoroolefin according to Item 12, wherein the chlorine-containing compound used as a starting material is $CF_3CCl=CH_2$ (HCFO-1233xf), and the fluoroolefin to be obtained is $CF_3CF=CH_2$ (HFO-1234yf).

Item 14. The process for producing a fluoroolefin according to any one of Items 1 to 10, wherein the chlorine-containing compound used as a starting material is at least one member selected from the group consisting of a chlorine-containing alkane represented by formula (2): $CX_3(CX_2)_nCH_2CHX_2$ and a chlorine-containing alkene represented by formula (4): $CX_3(CX_2)_nCH=CHX$, and the fluoroolefin to be obtained is a fluoroolefin represented by formula (6-2): $CF_3(CF_2)_nCH=CHF$, wherein n is an integer of 0 to 2.

Item 15. The process for producing a fluoroolefin according to Item 14, wherein the chlorine-containing compound used as a starting material is at least one member selected from the group consisting of $CCl_3CH=CHCl$ (HCO-1230zd) and $CF_3CH=CHCl$ (HCFO-1233zd), and the fluoroolefin to be obtained is $CF_3CH=CHF$ (HFO-1234ze).

Item 16. The process for producing a fluoroolefin according to Item 15, wherein the chlorine-containing compound used as a starting material is $CF_3CH=CHCl$ (HCFO-1233zd) and the fluoroolefin to be obtained is $CF_3CH=CHF$ (HFO-1234ze).

Hereinbelow, the process for producing a fluoroolefin of the present invention is specifically explained.

Starting Material

In the present invention, used as a starting material is at least one chlorine-containing compound selected from the group consisting of a chlorine-containing alkane represented by formula (1): $CX_3(CX_2)_nCClYCH_2Z$, wherein each X is independently F or Cl, and Y is H or F, and when Y is H, Z is Cl or F, and when Y is F, Z is H, and n is an integer of 0 to 2; a chlorine-containing alkane represented by formula (2): $CX_3(CX_2)_nCH_2CHX_2$, wherein each X is independently F or Cl, at least one X is Cl, and n is an integer of 0 to 2; a chlorine-containing alkene represented by formula (3): $CX_3(CX_2)_nCCl=CH_2$, wherein each X is independently F or Cl, and n is an integer of 0 to 2; a chlorine-containing alkene represented by formula (4): $CX_3(CX_2)_nCH=CHX$, wherein each X is independently F or Cl, at least one X is Cl, and n is an integer of 0 to 2; and a chlorine-containing alkene represented by formula (5): $CH_2XCCl=CX_2$, wherein each X is independently F or Cl.

By reacting such a chlorine-containing compound as a starting material with a fluorinating agent in the presence of a specific catalyst according to the conditions described below, it is possible to obtain a fluoroolefin represented by formula (6): $CF_3(CF_2)_nCA=CHB$, wherein one of A and B is F and the other is H, and n is an integer of 0 to 2, provided that n is 0 when the chlorine-containing alkene represented by formula (5) is used as a starting material, with high selectivity and a high conversion rate of the starting material.

Of the chlorine-containing compounds represented by formulae (1) to (5) above, compounds in which the number of carbon atoms is 3, i.e., n is 0, are preferred because they have an appropriate boiling point to perform a gas phase reaction. Preferable examples of the compounds in which n is 0 include $CCl_3CHClCH_2Cl$ (HCC-240db), $CF_3CHClCH_2Cl$ (HCFC-243db), and the like as the chlorine-containing alkane represented by formula (1); $CCl_3CH_2CHCl_2$ (HCC-240fa), $CF_3CH_2CHCl_2$ (HCFC-243fa), and the like as the chlorine-containing alkane represented by formula (2); $CCl_3CCl=CH_2$ (HCO-1230xf), $CF_3CCl=CH_2$ (HCFO-1233xf), and the like as the chlorine-containing alkene represented by formula (3); $CCl_3CH=CHCl$ (HCO-1230zd), $CF_3CH=CHCl$ (HCFO-1233zd), and the like as the chlorine-containing alkene represented by formula (4); and $CH_2ClCCl=CCl_2$ (HCO-1230xa), and the like as the chlorine-containing alkene represented by formula (5). Of these compounds, $CF_3CCl=CH_2$ (HCFO-1233xf) and $CF_3CH=CHCl$ (HCFO-1233zd) are particularly preferred. HCFO-1233xf is a known compound and can be easily obtained, for example, by adding chlorine to 3,3,3-trifluoro-1-propene to form HCFC-243db, and then subjecting the HCFC-243db to dehydrochlorination with alkali or the like.

In the present invention, the aforementioned starting materials can be used singly or in a combination of two or more.

Catalyst

In the process for producing fluoroalkene of the present invention, at least one member selected from the group consisting of chromium oxide, at least part of which is crystallized, and fluorinated chromium oxide obtained by fluorinating the chromium oxide can be used as a catalyst.

Chromium oxide used as a catalyst should be chromium oxide, at least part of which is crystallized. In particular, to increase the conversion rate of the starting material and the selectivity of the target fluoroolefin, the crystallinity is preferably about 30% or more, more preferably about 40% or more, even more preferably about 60% or more, and particularly preferably about 70% or more.

The crystallinity of the chromium oxide means the ratio of crystallized chromium oxide to all of the chromium oxide constituting the catalyst. A crystallinity of 100% indicates that substantially all of the chromium oxide is crystallized; a crystallinity of 50% indicates that 50 wt % of chromium oxide constituting the catalyst is crystallized.

In the present invention, crystallinity is determined according to the result of XRD measurement. Specifically, crystallinity means the ratio determined by comparison between the diffraction peak area of the all the crystal planes of the standard sample with that of the target chromium oxide, each area being calculated from a diffraction pattern obtained by XRD measurement performed under the same conditions. The standard sample substantially has a crystallinity of 100%. For example, when the diffraction peak area of all the crystal planes of the standard sample is 100 and the diffraction peak area of all the crystal planes of the measurement target chromium oxide is 50, the crystallinity is 50%.

Alternatively, the crystallinity can also be determined using an internal standard substance, which has a different diffraction pattern from that of the chromium oxide. Specifically, the crystallinity can be determined by comparison of the relative value of the diffraction peak area of all the crystal planes of the chromium oxide having a substantial crystallinity of 100% to that of the internal standard substance with the relative value of the diffraction peak area of all the crystal planes of the measurement target chromium oxide to that of the internal standard substance. Amorphous chromium oxide does not show a substantial XRD diffraction peak.

Further, by adjusting, within the aforementioned crystallinity range, the average crystallite diameter of the crystallized chromium oxide and the specific surface area, etc., of the chromium oxide, at least part of which is crystallized and which is used as a catalyst in the present invention, a target fluoroolefin can be produced at a high conversion rate of the starting material and high selectivity.

The average crystallite diameter of the crystallized chromium oxide is not particularly limited, and generally about 50 nm or less, preferably about 40 nm or less, and more preferably about 35 nm or less. The lower limit of the average crystallite diameter is not particularly limited, and it may be about 2 nm or more, preferably about 10 nm or more, and more preferably about 20 nm or more.

In the present specification, the average crystallite diameter is the average of the crystallite diameters of crystal planes obtained according to Scherrer's equation ($D=K\lambda/B \cos \theta$, wherein D is the crystallite diameter, K is the Scherrer constant, $\lambda$ is the X-ray wavelength/Cu radiation source, B is the full width at half maximum, and $\theta$ is half of diffraction angle $2\theta$), using the full width at half maximum of the XRD diffraction pattern of the chromium oxide.

Further, the chromium oxide, at least part of which is crystallized, preferably has a BET specific surface area of about 10 m$^2$/g or more.

Regarding the composition of the chromium oxide, at least part of which is crystallized, the crystallized chromium oxide portion can be represented by formula $Cr_2O_3$. The amorphous chromium oxide portion can be, for example, represented by composition formula $CrO_m$ ($1.5 \leq m \leq 3$). Of these, m is preferably in the range of $1.5 < m < 3$, more preferably $1.8 \leq m \leq 2.5$, and even more preferably $2.0 \leq m \leq 2.3$. Further, a mixture of chromium oxides having a different m value in the aforementioned m range can also be used.

The process for producing chromium oxide, at least part of which is crystallized, is not particularly limited. For example, the chromium oxide can be obtained by calcinating chromium hydroxide obtained by a coprecipitation method. In this case, by appropriately setting the calcination conditions, the crystallinity of chromium oxide or the crystallite diameter of crystallized chromium oxide can be adjusted. Specific examples of the catalyst production method are shown below.

First, for a coprecipitation method, an aqueous solution of chromium salt (chromium nitrate, chromium chloride, chromium alum, chromium sulfate, chromium acetate, or the like) and aqueous ammonia are mixed to obtain a precipitate of chromium hydroxide. For example, 10% aqueous ammonia is added dropwise to a 5.7% chromium nitrate aqueous solution in an amount about 1 to 1.2 equivalent per equivalent of chromium nitrate to obtain a precipitate of chromium hydroxide. The precipitate of chromium hydroxide is filtered, washed with distilled water, and dried. The drying may be performed in air at about 70° C. to 200° C. for about 1 to 100 hours. After the product is disintegrated into a powder, the resulting powder is calcined directly, or after being molded into a desired size and shape. In molding, for example, graphite is mixed as necessary in an amount of about 3 wt % or less, and is formed into a pellet with a tableting machine. The pellet may have, for example, a diameter of about 3.0 mm and a height about 3.0 mm.

The calcination can be performed in an inert gas flow, such as nitrogen, helium, and argon, an air flow, a water-vapor flow, an oxygen flow, or a mixed gas flow in which oxygen and the aforementioned inert gas are adjusted to have an appropriate composition. By selecting an atmosphere gas for the calcination and adjusting the calcination temperature, the crystallinity of the chromium oxide after calcination and the crystallite diameter can be adjusted.

For the relation between the calcination conditions and the crystallinity of chromium oxide or the crystallite diameter, in general, the greater the calcination temperature and the calcination time, the greater the crystallinity and the crystallite diameter; and the greater the concentration of a gas component having oxidizing ability in an atmosphere gas, e.g., oxygen, the greater the crystallinity and the crystallite diameter. Further, the lower the temperature increase rate during calcination, the more moderate the crystal growth, thus increasing the crystallite diameter. Therefore, for example, to increase the crystallinity and decrease the crystallite diameter, a method can be used in which an inert gas such as $N_2$ is used as an atmosphere gas and the calcination is performed in a very short time by setting the calcination temperature high and raising the temperature increase rate. Since these conditions vary depending on the heating device or calcination apparatus used in calcination, and the amount of the catalyst to be calcined, appropriate calcination conditions need to be determined according to a specific calcination method.

Amorphous chromium oxide, for example, can be obtained by calcinating a pellet that has been molded after drying and disintegrating the chromium hydroxide obtained by the coprecipitation method, described above, at about 380° C. to 460° C. for about 1 to 5 hours in an inert gas flow such as a nitrogen flow. It is possible to obtain chromium oxide having a crystallinity of about 40% and a crystallite diameter (crystallized portion) of about 34 nm when a product in the form of powder obtained by drying and disintegrating chromium hydroxide, which is obtained by the coprecipitation method, is introduced into a heat-resistant container such as a melting pot, allowed to stand in a heating furnace, and calcined at 350° C. for 2 hours in an air flow. Similarly, it is possible to obtain chromium oxide having a substantial crystallinity of about 100% and an average crystallite diameter of about 35 nm when a product in the form of powder obtained by drying and disintegrating chromium hydroxide, which is obtained by the coprecipitation method, is introduced into a heat-resistant container such as a melting pot, allowed to stand in a heating furnace, and calcined at 700° C. for 2 hours in an air flow.

The combination of these conditions and the crystallinity or the crystallite diameter is an example, and a desired crystallinity and crystallite diameter can be adjusted by appropriately selecting the kind of atmosphere gas, calcination temperature, calcination time, temperature increase rate to reach the calcination temperature, chromium oxide form (e.g., powder or molded product), furnace used in calcination, container used during calcination, filling conditions in the container, etc.

Further, it is possible to mix two or more different types of chromium oxide, each having a different crystallinity and a different crystallite diameter adjusted according to the above method or the like.

The fluorinated chromium oxide used as a catalyst is obtained by fluorinating the chromium oxide, which satisfies the above conditions and at least part of which is crystallized. The fluorinated chromium oxide can be produced by gradually promoting fluorination of the chromium oxide during the reaction of a chlorine-containing compound used as a starting material and a fluorinating agent; however, until the chromium oxide catalyst is sufficiently fluorinated, a chlorine-containing compound used as a starting material, a target product, or an intermediate may cause a side reaction, which sometimes reduces the yield of the target product or the catalyst activity by accumulation of a reaction inhibitor on the catalyst. For this reason, fluorinated chromium oxide produced by fluorinating the chromium oxide before the reaction is preferably used. To fluorinate the chromium oxide before the reaction, the chromium oxide placed in a reaction container may be, for example, brought into contact with a fluorinating agent before the reaction of a chlorine-containing compound and the fluorinating agent. The specific fluorination conditions in this case are such that the chromium oxide is heated at about 100° C. to 460° C. in an anhydrous hydrogen fluoride flow.

Although the degree of fluorination of fluorinated chromium oxide is not particularly limited, for example, the fluorinated chromium oxide having a fluorine content of about 10 to 30 wt % is preferably used.

Further, chromium oxide, at least part of which is fluorinated, and fluorinated chromium oxide obtained by fluorinating the chromium oxide may contain metal element(s) other than chromium. The amount of the metal element(s) other than chromium is not particularly limited, and is about 1 to 20 wt % based on the total catalyst.

The catalyst of the present invention may be supported on a carrier. The carrier is not particularly limited, and examples include $SiO_2$, $Al_2O_3$, zeolite, activated carbon, zirconium oxide, and the like.

Reaction Process

In the present invention, the above-mentioned starting material and the fluorinating agent should be reacted in a gas phase in the presence of at least one catalyst selected from the group consisting of chromium oxide, at least part of which is crystallized, and fluorinated chromium oxide obtained by fluorinating the chromium oxide.

Usable fluorinating agents are fluorine gas, anhydrous hydrogen fluoride, etc.; anhydrous hydrogen fluoride is preferred.

In a process of reacting the starting material and the fluorinating agent in a gas phase, the starting material and the fluorinating agent are in a gaseous state when the starting material and the fluorinating agent are brought into contact with the catalyst. When the starting material and the fluorinating agent are supplied, they may be in a liquid state. For example, when the starting material is liquid at ordinal temperature and normal pressure, the starting material is vaporized by a vaporizer (vaporization region), then allowed to pass through a preheating region, and supplied to a mixing region in which the starting material is brought into contact with the catalyst. Thus, the reaction can be carried out in a gas phase. Alternatively, the starting material is supplied to a reactor in a liquid state, while a catalyst layer placed in the reactor is heated above the vaporization temperature of the starting material. When the starting material arrives at a region for reaction with the fluorinating agent, the starting material is vaporized and reacted.

The proportion of the fluorinating agent and the starting material to be introduced is not particularly limited. However, when the amount of the fluorinating agent is too low, the conversion rate of the starting material tends to decrease. In contrast, when the proportion of the fluorinating agent is too high, productivity is reduced because the amount of the fluorinating agent removed increases after the reaction. Considering these points, when anhydrous hydrogen fluoride is used as the fluorinating agent, in general, anhydrous hydrogen fluoride is preferably used in an amount of 5 equivalents or more, and more preferably 5 to 20 equivalents or more per equivalent of the starting material.

A specific example of the embodiment of the process of the present invention is a process in which the above-mentioned catalyst is placed in a tubular flow-type reactor, and a chlorine-containing compound, which is used as a starting material, and the fluorinating agent are introduced into the reactor.

The reactor is preferably made of a material resistant to the corrosive action of hydrogen fluoride, such as Hastelloy, Inconel, or Monel.

The above-mentioned starting material may be directly supplied to the reactor; alternatively, nitrogen, helium, argon, or another gas that is inert to the starting material and catalyst may be present together. The concentration of the inert gas may be about 0 to 80 mol % based on the amounts of the inert gas and the gas components introduced into the reactor, i.e., the chlorine-containing compound and the fluorinating agent.

In the process of the present invention, when the reaction is performed in the presence of oxygen, a decrease in catalytic activity can be prevented and the target fluoroolefin can be produced continuously for a long period of time and with high selectivity. Although the method of performing the reaction in the presence of oxygen is not particularly limited, oxygen may be generally supplied to the reactor together with the chlorine-containing compound used as a starting material.

The amount of oxygen supplied is, although not particularly limited, preferably about 0.001 mol or more, and more preferably about 0.001 to 0.3 mol, per mol of the chlorine-containing compound used as a starting material.

In particular, in order to achieve the effect of improving the starting material conversion rate while maintaining high selectivity, it is preferable to use as a catalyst a chromium oxide having a crystallinity of 30% or more and an average crystallite diameter of about 10 to 40 nm, or a fluorinated chromium oxide obtained by fluorinating the chromium oxide, and to supply oxygen in an amount as relatively small as about 0.001 to 0.3 mol per mol of the chlorine-containing compound used as a starting material. Especially, it is preferable to use as a catalyst a chromium oxide having a crystallinity of 60% or more and an average crystallite diameter of about 20 to 35 nm, or a fluorinated chromium oxide obtained by fluorinating the chromium oxide, and to supply oxygen in an amount as relatively small as about 0.001 to 0.3 mol per mol of the chlorine-containing compound used as a starting material. Performing the reaction in the presence of oxygen under such conditions can effectively provide an effect of preventing catalyst deterioration and effectively reduce the amount of $CO_2$ generated as a by-product. Accordingly, it is possible to solve the problem of reduction in purification efficiency due to the presence of non-condensable gas in the purification step, which is caused by the presence of excess oxygen. The danger of an explosion occurring when the starting material or generated gas is flammable can also be avoided.

In contrast, the use of an amorphous chromium oxide catalyst leads to the generation of a large amount of by-product such as carbon dioxide, thus relatively reducing the yield of the target product when compared under the same reaction conditions using the same oxygen introduction amount.

Further, in the process of the present invention, by performing the reaction in the presence of molecular chlorine, as necessary, a decrease in catalytic activity can be prevented, thus obtaining the target fluoroolefin continuously for a long period of time and with high yield. Although the method of performing the reaction in the presence of molecular chlorine is not particularly limited, molecular chlorine is generally supplied to the reactor together with the chlorine-containing compound used as a starting material.

The amount of molecular chlorine supplied is preferably about 0.001 to 0.05 mol, and more preferably about 0.002 to 0.03 mol, per mol of the chlorine-containing compound used as a starting material.

In addition, according to the process of the present invention, when the chlorine-containing compound used as a starting material and the fluorinating agent are reacted in a gas phase while controlling the moisture content of the reaction system to a low level, a decrease in catalytic activity is prevented, resulting in production of the target fluoroolefin continuously for a long period of time and with high yield. In this case, examples of the moisture of the reaction system include moisture contained in the chlorine-containing compound, which is used as a starting material, moisture contained in the fluorinating agent, and moisture contained in the optional components, such as molecular chlorine, oxygen, and inert gas. The total amount of such moisture is preferably controlled to the amount of 300 ppm or less, and more preferably 100 ppm or less, based on the weight of the chlorine-containing compound used as a starting material.

The method of reducing the moisture content of the reaction system is not particularly limited, and the chlorine-containing compound, which is used as a starting material, hydrogen fluoride, and other additives may be dehydrated by a known method before use in the reaction. For example, these components are subjected to the reaction after dehydration, or dehydrated and continuously supplied to the reaction system. Such methods can be suitably applied.

As a method for dehydrating the chlorine-containing compound used as a starting material, a distillation method and a method using a dehydrating agent can be applied. Considering efficiency, a moisture removing method using a dehydrating agent is preferred. As the moisture removing method using a dehydrating agent, a method in which moisture is adsorbed using zeolite is preferred. The form of zeolite is not particularly limited, and zeolite in the form of powder, granule, or agglomerate can be used. Zeolite having a pore size of about 2.0 to 6.0 Å can be used. The method of bringing the chlorine-containing compound into contact with zeolite is not particularly limited; however, it is generally preferred from the viewpoint of efficiency to pass the chlorine-containing compound in a gas or liquid form through a container filled with zeolite.

Even without separately providing a container filled with a dehydrating agent, the reaction can be performed with a reduced moisture content in the reaction system by providing a filling layer of a dehydrating agent before a catalyst filling layer in a reaction apparatus (tubular reactor), and passing the starting material introduced in the reaction apparatus (tubular reactor) through the filling layer of the dehydrating agent and then the catalyst layer. Although the location of the filling layer of the dehydrating agent is not particularly limited, it is preferable to provide the layer at a portion having a temperature of 100° C. or less and before the catalyst layer because moisture adsorbed from the dehydrating agent is desorbed at a temperature exceeding 100° C.

As a method for dehydrating the fluorinating agent, a distillation method, etc., can be applied.

Specific dehydration conditions may be determined by performing a preliminary experiment according to the moisture content in the starting material, the additive components, or the like, and the type and the structure of the device used so that the amount of moisture of the reaction system attains a desired level.

Regarding the reaction temperature, a temperature too low results in a great reduction in the conversion rate of the starting material, while a temperature too high leads to an increase in the production of by-product impurities and a decrease in selectivity. Considering these points, the reaction temperature is preferably about 200° C. to 550° C., and more preferably about 250° C. to 380° C.

The pressure during the reaction is, although not particularly limited, preferably in the range of atmospheric pressure to 3 MPa, and more preferably in the range of atmospheric pressure to about 0.3 MPa. When the pressure during the reaction is increased, the conversion rate of the starting material may be enhanced; however, a pressure too high is not preferred, because safety risks and economic risks are increased, and a fluorine-containing alkane in which hydrogen fluoride is added to a resulting target fluoroolefin is obtained in a large amount; consequently, the selectivity of the desired product may be reduced.

Although the reaction time is not particularly limited, for example, contact time $W/F_0$ represented by the ratio of the amount of catalyst used W (g) to the total flow rate $F_0$ (flow rate at 0° C. and 0.1 MPa: mL/sec) of the starting material gas introduced into the reaction system is preferably in the range of 0.1 to 100 g·sec/NmL, and more preferably about 5 to 50 g·sec/NmL. The total flow rate of the starting material gas in this case refers to the total of the flow rate of the chlorine-containing compound and fluorinating agent, and the flow rate of, when used, inert gas, molecular chlorine, oxygen, etc.

Reaction Product

According to the process described above, the fluorination reaction of the above starting material results in production of a fluoroolefin represented by formula (6): $CF_3(CF_2)_n$CA=CHB, wherein one of A and B is F, and the other is H, and n is an integer of 0 to 2, provided that n is 0 when a chlorine-containing alkene represented by formula (5) is used as a starting material, with a high conversion rate of the starting material and good selectivity.

More specifically, when the starting material is at least one chlorine-containing compound selected from the group consisting of a chlorine-containing alkane represented by formula (1): $CX_3(CX_2)_n$CClYCH$_2$Z, a chlorine-containing alkene represented by formula (3): $CX_3(CX_2)_nCCl=CH_2$, and a chlorine-containing alkene represented by formula (5): $CH_2XCCl=CX_2$, it is possible to obtain a compound of formula (6) wherein A is F, and B is H, that is, a compound of formula (6-1): $CF_3(CF_2)_nCF=CH_2$, wherein n is an integer of 0 to 2, provided that n is 0 when a chlorine-containing alkene represented by formula (5) is used as a starting material. Further, when the starting material is at least one chlorine-containing compound selected from the group consisting of a chlorine-containing alkane represented by formula (2): $CX_3(CX_2)_nCH_2CHX_2$ and a chlorine-containing alkene represented by formula (4): $CX_3(CX_2)_nCH=CHX$, it is possible to obtain a compound of formula (6) wherein A is H, and B is F, that is, a fluoroolefin represented by formula (6-2): $CF_3(CF_2)_nCH=CHF$ wherein n is an integer of 0 to 2.

For example, when the starting material is $CF_3CHClCH_2Cl$ (HCFC-243db), which is a chlorine-containing alkane represented by formula (1), $CCl_3CCl=CH_2$ (HCO-1230xf) or $CF_3CCl=CH_2$ (HCFO-1233xf), which is a chlorine-containing alkene represented by formula (3), $CH_2ClCCl=CCl_2$ (HCO-1230xa)), which is a chlorine-containing alkene represented by formula (5), or the like, it is possible to obtain 2,3,3,3-tetrafluoropropene represented by formula: $CF_3CF=CH_2$ (HFO-1234yf). The resulting product may also contain 1,3,3,3-tetrafluoropropene represented by formula: $CF_3CH=CHF$ (HFO-1234ze), together with HFO-1234yf. Moreover, when the starting material is $CCl_3CH=CHCl$ (HCO-1230zd) or $CF_3CH=CHCl$ (HCFO-1233zd), which is a chlorine-containing alkene represented by formula (4), or the like, it is possible to obtain 1,3,3,3-tetrafluoropropene represented by formula: $CF_3CH=CHF$ (HFO-1234ze).

Furthermore, a mixture of a fluoroolefin represented by formula (6-1) and a fluoroolefin represented by formula (6-2) can be obtained when the starting material is a mixture of at least one chlorine-containing compound selected from the group consisting of a chlorine-containing alkane represented by formula (1): $CX_3(CX_2)_nCClYCH_2Z$, a chlorine-containing alkene represented by formula (3): $CX_3(CX_2)_nCCl=CH_2$, and a chlorine-containing alkene represented by formula (5): $CH_2XCCl=CX_2$, with at least one chlorine-containing compound selected from the group consisting of a chlorine-containing alkane represented by formula (2): $CX_3(CX_2)_nCH_2CHX_2$ and a chlorine-containing alkene represented by formula (4): $CX_3(CX_2)_nCH=CHX$.

The reaction product can be recovered after purification by distillation or the like. Further, unreacted fluorinating agent, starting materials, or intermediates obtained from the outlet of the reactor can be recycled by returning them to the reactor after separation and purification. Because of the recycling of the unreacted starting materials and fluorinating agent, high productivity can be maintained even if the conversion rate of the starting material is not high.

In the production of 2,3,3,3-tetrafluoropropene (HFO-1234yf), 1,1,1,2,2-pentafluoropropane (HFC-245cb), which is a main component of the by-product contained in the product, can be easily converted into 2,3,3,3-tetrafluoropropene (HFO-1234yf) by hydrogen fluoride-elimination reaction; therefore, 1,1,1,2,2-pentafluoropropane (HFC-245cb) contained in the product is also a useful compound. Moreover, in the production of 1,3,3,3-tetrafluoropropene (HFO-1234ze), 1,1,1,3,3-pentafluoropropane (HFC-245fa), which is a main component of the by-product contained in the product, can be easily converted into 1,3,3,3-tetrafluoropropene (HFO-1234ze) by hydrogen fluoride-elimination reaction; therefore, 1,1,1,3,3-pentafluoropropane (HFC-245fa) contained in the product is also a useful compound.

Advantageous Effects of Invention

According to the process of the present invention, the target fluoroolefin can be obtained from at least one chlorine-containing compound represented by a specific formula, which is used as a starting material, with a high conversion rate of the starting material and good selectivity by using chromium oxide, at least part of which is crystallized, or fluorinated chromium oxide obtained by fluorinating the chromium oxide as a catalyst.

Therefore, the process of the present invention is industrially advantageous as a process for producing fluoroolefins by fluorination of chlorine-containing compounds.

DESCRIPTION OF EMBODIMENTS

The present invention is described in more detail below with reference to Production Examples of catalysts used in the present invention and Examples of the present invention.

Production Example 1 (Preparation of Chromium Oxide Catalyst Precursor)

10% aqueous ammonia (118 g) was added to 900 g of an aqueous solution in which 77 g of chromium nitrate nonahydrate was dissolved to precipitate chromium hydroxide by neutralization. The chromium hydroxide precipitate was collected by filtration with a Buchner funnel, washed with water (3 L), and filtered, thereby obtaining chromium hydroxide.

Production Example 2 (Preparation of Amorphous Chromium Oxide Catalyst)

The solid obtained in Production Example 1 was dried at 120° C. for 12 hours. After making the solid into a powder, graphite was added in an amount of 3% based on the total weight, and the resulting mixture was molded into pellets (2-mm dia.×2 mm) and calcined at 400° C. in a nitrogen flow for 2 hours, thereby obtaining chromium oxide.

Figure 1:
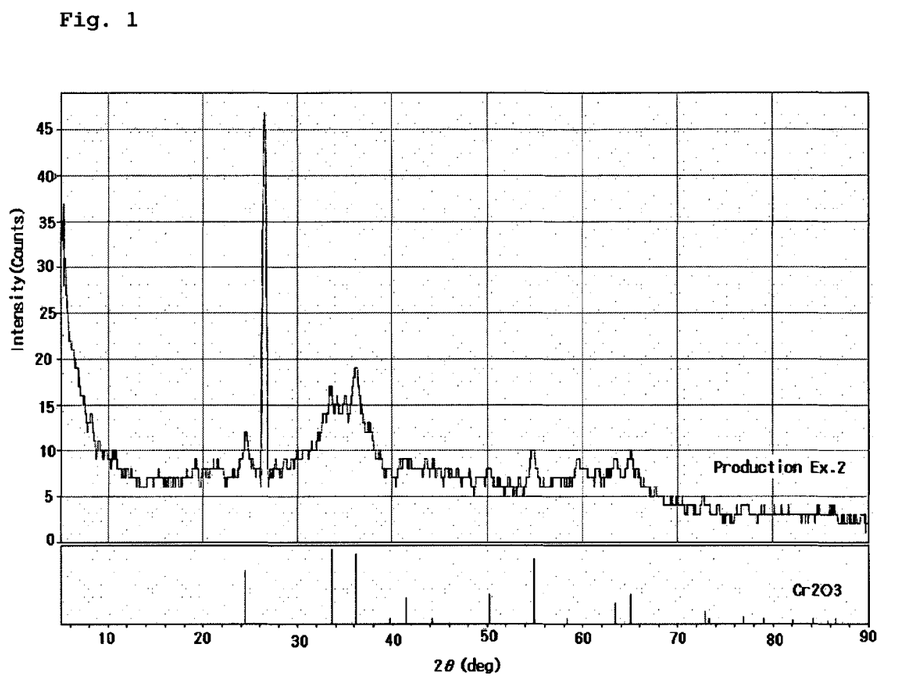
FIG. 1 shows an XRD pattern of the amorphous chromium oxide obtained in Production Example 2, and a XRD pattern index of $Cr_2O_3$ crystal.

According to the XRD pattern of the oxide powder, the diffraction pattern derived from crystal was not observed, and the oxide was amorphous. In FIG. 1, the diffraction peak around 2θ=26.5° indicated added graphite.

Production Example 3 (Preparation of Partially Crystallized Chromium Oxide Catalyst: Crystallinity: 38%, Average Crystallite Diameter: 32.3 nm)

The solid obtained in Production Example 1 was dried at 120° C. for 12 hours. After making the solid into a powder, the powder was calcined at 350° C. in an air flow for 3 hours, thereby obtaining chromium oxide.

According to the XRD pattern of the oxide powder, the diffraction pattern derived from α-Cr$_2$O$_3$ was observed, the crystallinity obtained from the pattern area was 38%, and the oxide was chromium oxide containing a crystal portion and an amorphous portion. Based on the full width at half maximum, the crystallized chromium oxide had an average crystallite diameter of 32.3 nm.

Production Example 4 (Preparation of Partially Crystallized Chromium Oxide Catalyst: Crystallinity: 62%, Average Crystallite Diameter: 25.3 nm)

The solid obtained in Production Example 1 was dried at 120° C. for 12 hours. After making the solid into a powder, the powder was calcined at 400° C. in an air flow for 3 hours, thereby obtaining chromium oxide.

According to the XRD pattern of the oxide powder, the diffraction pattern derived from α-Cr$_2$O$_3$ was observed, the crystallinity obtained from the pattern area was 62%, and the oxide was chromium oxide containing a crystal portion and an amorphous portion. Based on the full width at half maximum, the crystallized chromium oxide had an average crystallite diameter of 25.3 nm.

Production Example 5 (Preparation of Partially Crystallized Chromium Oxide Catalyst: Crystallinity: 73%, Average Crystallite Diameter: 24.0 nm)

The solid obtained in Production Example 1 was dried at 120° C. for 12 hours. After making the solid into a powder, the powder was calcined at 550° C. in an air flow for 3 hours, thereby obtaining chromium oxide.

According to the XRD pattern of the oxide powder, the diffraction pattern derived from α-Cr$_2$O$_3$ was observed, the crystallinity obtained from the pattern area was 73%, and the oxide was chromium oxide containing a crystal portion and an amorphous portion. Based on the full width at half maximum, the crystallized chromium oxide had an average crystallite diameter of 24.0 nm.

Production Example 6 (Preparation of Crystallized Chromium Oxide Catalyst: Crystallinity: 100%, Average Crystallite Diameter: 34.3 nm)

The solid obtained in Production Example 1 was dried at 120° C. for 12 hours. After making the solid into a powder, the powder was calcined at 700° C. in an air flow for 3 hours, thereby obtaining chromium oxide.

Figure 2:
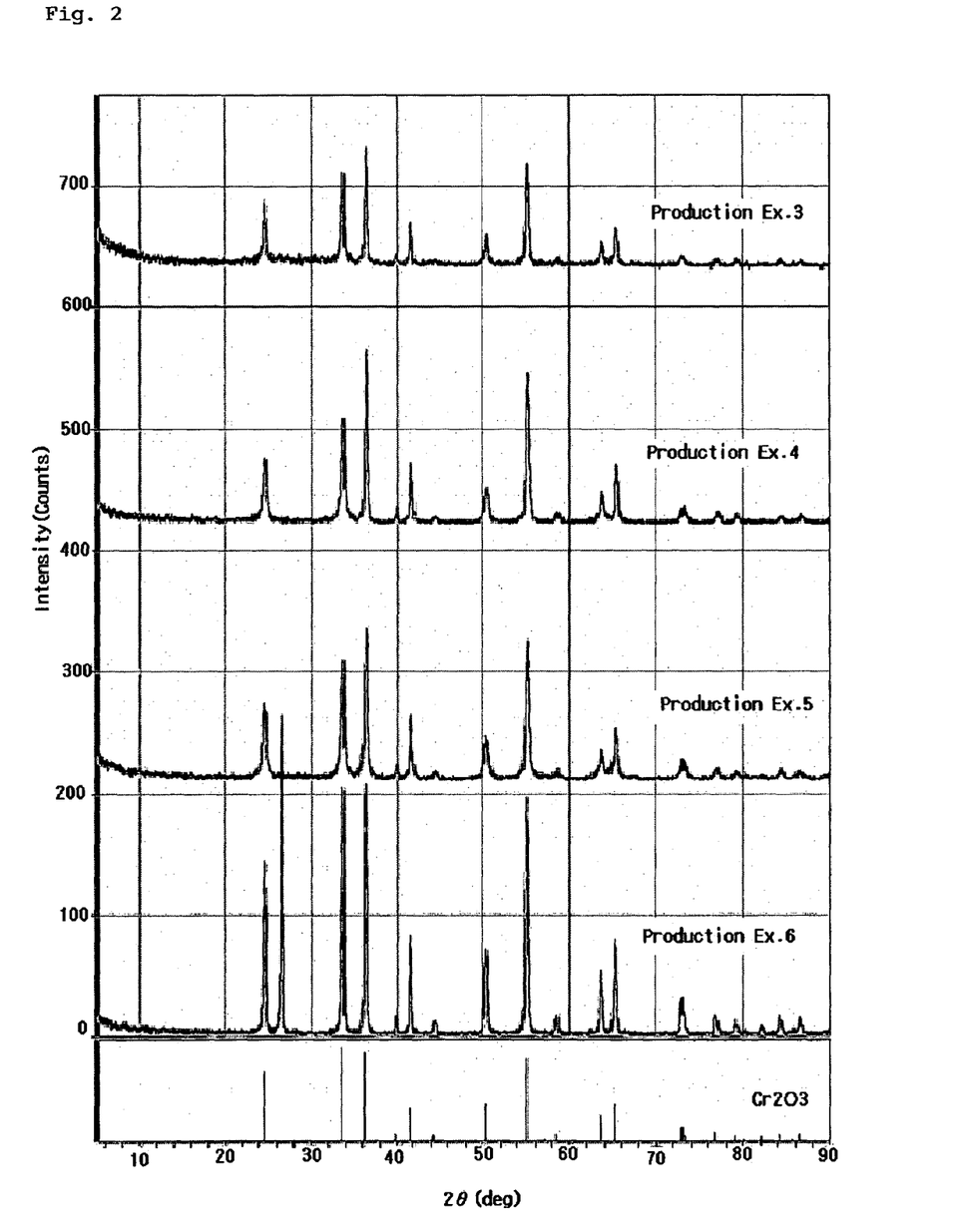
FIG. 2 shows XRD patterns of the chromium oxide, at least part of which is crystallized, obtained in Production Examples 3 to 7, and a XRD pattern index of $Cr_2O_3$ crystal.

According to the XRD pattern of the oxide powder, the diffraction pattern derived from α-Cr$_2$O$_3$ was observed, the crystallinity obtained from the pattern area was 100%, and the oxide was crystalline chromium oxide. Based on the full width at half maximum, the crystallized chromium oxide had an average crystallite diameter of 34.3 nm. In FIG. 2, the diffraction peak around 2θ=26.5° indicated graphite added for molding.

Examples 1 to 4

Each of the chromium oxide catalysts (7.0 g) prepared in Production Examples 3 to 6 was placed in a 1 m-long tubular Hastelloy reactor.

The reactor was heated, and the catalyst was first fluorinated by introducing nitrogen gas and hydrogen fluoride gas. To avoid the deterioration of the catalyst due to the rapid reaction of the catalyst and hydrogen fluoride, the reaction was gradually performed in two steps using heating temperatures and introduction rates shown below.

Step 1: Nitrogen gas at 450 Nml/min (flow rate at 0° C. and 0.1 Mpa, the same as below) and hydrogen fluoride gas at 50 Nml/min for 1 hour at 200° C.

Step 2: Nitrogen gas at 100 Nml/min, hydrogen fluoride gas at 400 Nml/min for 1 hour at 330° C.

Between Steps 1 and 2, it took 1.5 hours to change the temperature and the flow rate of the nitrogen gas and the hydrogen fluoride gas.

The temperature of the reactor was raised to 350° C., and anhydrous hydrogen fluoride gas and oxygen gas were supplied to the reactor at flow rates of 42 NmL/min and 0.42 NmL/min, respectively, and maintained for 0.5 hours. Thereafter, CF$_3$CCl=CH$_2$ (HCFC-1233xf) gas was supplied at a flow rate of 4.2 NmL/min. About 30 hours later, the effluent gas from the reactor was analyzed by gas chromatography.

Table 1 shows the results. Since HFC-245cb in the product is a useful compound that can be converted into HFO-1234yf by a hydrogen fluoride elimination reaction, Table 1 also shows the total selectivity of HFO-1234yf and HFC-245cb. In addition, Table 1 shows the conversion rate of the starting material, and the total yield of HFO-1234yf and HFC-245cb based on the starting material, calculated on the total selectivity of HFO-1234yf and HFC-245cb.

The symbols shown in the table indicate the following compounds:

| 1233xf | CF$_3$CCl=CH$_2$ |
| 1234yf | CF$_3$CF=CH$_2$ |
| 245cb | CF$_3$CF$_2$CH$_3$ |
| 1234ze | CF$_3$CH=CHF |
| 1233zd | CF$_3$CH=CHCl |

Comparative Example 1

Fluorination treatment of a catalyst and fluorination reaction were performed as in Example 1, except that the amorphous chromium oxide obtained in Production Example 2 was used as a catalyst. Table 1 shows the results.

TABLE 1

|  | Ex. 1 | Ex. 2 | Ex. 3 | Ex. 4 | Comp. Ex. 1 |
| --- | --- | --- | --- | --- | --- |
| Catalyst preparation example | Prod. Ex. 3 | Prod. Ex. 4 | Prod. Ex. 5 | Prod. Ex. 6 | Prod. Ex. 2 |
| Crystallinity (%) | 38 | 62 | 73 | 100 | 0 |
| Specific surface area (m$^2$/g) | 20 | 24 | 11 | 10 | 203 |
| Average crystallite diameter (nm) | 32.3 | 25.3 | 24.0 | 34.3 | — |
| 1233xf conversion (GC %) | 11 | 20 | 20 | 20 | 17 |
| 1234yf selectivity (GC %) | 68 | 68 | 67 | 68 | 66 |
| 245cb selectivity (GC %) | 23 | 22 | 23 | 23 | 23 |

TABLE 1-continued

|  | Ex. 1 | Ex. 2 | Ex. 3 | Ex. 4 | Comp. Ex. 1 |
|---|---|---|---|---|---|
| 1234ze selectivity (GC %) | 0.6 | 3.4 | 3.9 | 4.3 | 2.8 |
| 1233zd selectivity (GC %) | 0.5 | 1.4 | 1.6 | 1.3 | 0.9 |
| $CO_2$ selectivity (GC %) | 2.6 | 1.8 | 1.7 | 0.9 | 4.2 |
| Other by-product selectivity (GC %) | 5.3 | 3.4 | 2.8 | 2.5 | 3.1 |
| 1234yf + 245cb selectivity (GC %) | 91 | 90 | 90 | 91 | 89 |
| 1234yf + 245cb total yield (%) | 10 | 18 | 18 | 18 | 15 |

As is clear from Table 1, Examples 2 to 4, in which partially or wholly crystallized chromium oxide satisfying the conditions that the crystalli degree was 60% or more, the average crystallite diameter was 24 to 35 nm, and the specific surface area was 10 m²/g or more was used as a catalyst, showed high levels in the selectivity and the total yield of HFO-1234yf and HFC-245cb, which are useful compounds, as well as a high HCFC-1233xf conversion rate compared to those of Comparative Example 1, in which amorphous chromium oxide was used as a catalyst. In particular, Example 4, in which chromium oxide having a crystallinity of 100% was used as a catalyst, showed the highest 1234yf+245cb selectivity, i.e., 91%; thus, an excellent effect was attained.

In the aforementioned Examples and in Comparative Example 1, the highest HCFC-1233xf conversion rate was 20%, and thus an unreacted starting material will be recycled and reused in the actual process. Accordingly, the greater the 1234yf+245cb selectivity, the greater the yield of the target product in the actual process. When compared under the same conditions, the greater the 1233xf conversion rate, the lower the equipment costs. This is because the recycled amount of an unreacted starting material is reduced.

Consequently, the processes of Examples 2 to 4 in which chromium oxide with a crystallinity of 60% or more, an average crystallite diameter of 24 to 35 nm, and a surface area of 10 m²/g or more was used as a catalyst, are industrially advantageous because they have a high 1233xf conversion rate and high 1234yf+245cb selectivity.

Example 1, in which chromium oxide having a crystallinity of 38% was used as a catalyst, showed a low HCFC-1233xf conversion rate and a low total yield of HFO-1234yf and HFC-245cb compared to Comparative Example 1, but had high HFO-1234yf and HFC-245cb selectivity. Therefore, in the actual process, in which the starting material is reused, the total yield of HFO-1234yf and HFC-245cb is higher than in a process in which an amorphous chromium oxide is used as a catalyst; thus, the process of Example 1 is industrially advantageous

The invention claimed is:

1. A process for producing a fluoroolefin comprising:
   reacting a fluorinating agent and a chlorine-containing compound in a gas phase in the presence of at least one catalyst selected from the group consisting of chromium oxide, at least part of which is crystallized, and fluorinated chromium oxide obtained by fluorinating the chromium oxide,
   wherein the chlorine-containing compound is a chlorine-containing alkene of formula (3): $CX_3(CX_2)_n CCl=CH_2$, wherein each X is independently F or Cl, and n is an integer of 0 to 2, and
   the fluoroolefin is a compound of formula (6): $CF_3(CF_2)_n CA=CHB$, wherein one of A and B is F and the other is H, and n is an integer of 0 to 2.

2. The process for producing a fluoroolefin according to claim 1, wherein the chromium oxide, at least part of which is crystallized, has a crystallinity of 30% or more.

3. The process for producing a fluoroolefin according to claim 1, wherein the chromium oxide, at least part of which is crystallized, has a crystallinity of 60% or more.

4. The process for producing a fluoroolefin according to claim 1, wherein the chromium oxide, at least part of which is crystallized, has a crystallinity of 70% or more.

5. The process for producing a fluoroolefin according to claim 1, wherein the crystallized chromium oxide has an average crystallite diameter of 50 nm or less.

6. The process for producing a fluoroolefin according to claim 1, wherein the chromium oxide has a specific surface area of 10 m²/g or more.

7. The process for producing a fluoroolefin according to claim 1, wherein the at least one catalyst is supported on a carrier.

8. The process for producing a fluoroolefin according to claim 7, wherein the carrier is at least one member selected from the group consisting of $SiO_2$, $Al_2O_3$, zeolite, activated carbon, and zirconium oxide.

9. The process for producing a fluoroolefin according to claim 1, wherein the catalyst comprising the chromium oxide, at least part of which is crystallized, is fluorinated, and then the chlorine-containing compound is reacted with the fluorinating agent.

10. The process for producing a fluoroolefin according to claim 1, wherein the fluorinating agent is anhydrous hydrogen fluoride.

11. The process for producing a fluoroolefin according to claim 1, wherein the fluoroolefin is a compound of formula (6-1): $CF_3(CF_2)_n CF=CH_2$, wherein n is an integer of 0 to 2.

12. The process for producing a fluoroolefin according to claim 11, wherein the chlorine-containing compound used as a starting material is at least one member selected from the group consisting of $CCl_3CCl=CH_2$ (HCO-1230xf) and $CF_3CCl=CH_2$ (HCFO-1233xf), and the fluoroolefin is $CF_3CF=CH_2$ (HFO-1234yf).

13. The process for producing a fluoroolefin according to claim 12, wherein the chlorine-containing compound used as a starting material is $CF_3CCl=CH_2$ (HCFO-1233xf), and the fluoroolefin is $CF_3CF=CH_2$ (HFO-1234yf).

* * * * *